(12) United States Patent
Davis, III et al.

(10) Patent No.: US 7,043,288 B2
(45) Date of Patent: May 9, 2006

(54) APPARATUS AND METHOD FOR SPECTROSCOPIC ANALYSIS OF TISSUE TO DETECT DIABETES IN AN INDIVIDUAL

(75) Inventors: Herbert T. Davis, III, Corrales, NM (US); Robert K. Rowe, Corrales, NM (US); Stephen J. Vanslyke, Albuquerque, NM (US)

(73) Assignee: InLight Solutions, Inc., Albuquerque, NM (US)

( * ) Notice: Subject to any disclaimer, the term of this patent is extended or adjusted under 35 U.S.C. 154(b) by 0 days.

(21) Appl. No.: 10/116,272

(22) Filed: Apr. 4, 2002

(65) Prior Publication Data

US 2003/0191378 A1 Oct. 9, 2003

(51) Int. Cl.
*A61B 5/00* (2006.01)

(52) U.S. Cl. .................... 600/310; 600/316
(58) Field of Classification Search ........ 600/309–310, 600/319, 316, 473, 476, 365
See application file for complete search history.

(56) References Cited

U.S. PATENT DOCUMENTS

| | | | |
|---|---|---|---|
| 4,094,609 A | 6/1978 | Fujii et al. |
| 4,653,880 A | 3/1987 | Sting et al. |
| 4,655,225 A | 4/1987 | Dähne et al. |
| 4,661,706 A | 4/1987 | Messerschmidt et al. |
| 4,684,255 A | 8/1987 | Ford |
| 4,712,912 A | 12/1987 | Messerschmidt |
| 4,730,882 A | 3/1988 | Messerschmidt |
| 4,853,542 A | 8/1989 | Milosevic et al. |
| 4,857,735 A | 8/1989 | Noller |
| 4,859,064 A | 8/1989 | Messerschmidt et al. |
| 4,867,557 A | 9/1989 | Takatani et al. |
| 4,882,492 A | 11/1989 | Schlager |
| 4,883,351 A | 11/1989 | Weiss |
| 4,883,953 A | 11/1989 | Koashi et al. |
| 4,895,159 A | 1/1990 | Weiss |
| 4,975,581 A | 12/1990 | Robinson et al. |
| 5,007,423 A | 4/1991 | Branstetter et al. |

(Continued)

FOREIGN PATENT DOCUMENTS

EP 0-222-419 A2 * 2/1986

(Continued)

OTHER PUBLICATIONS

Anderson, Chad E. et al., "Fundamentals of Calibration Transfer Through Procrustes Analysis," *Applied Spectros.*, vol. 53, No. 10 (1999) p. 1268-1276.

(Continued)

*Primary Examiner*—Eric F. Winakur
(74) *Attorney, Agent, or Firm*—V. Gerald Grafe; David M. Crompton

(57) ABSTRACT

Apparatus and methods for spectroscopic analysis of human tissue to classify an individual as diabetic or non-diabetic, or to determine the probability, progression or level of diabetes in an individual. Tissue optical information of an individual, including at least a measurement of at least one wavelength or group of wavelengths indicative of glycosylated collagen content in tissue, is analyzed using multivariate techniques. The multivariate techniques include an algorithm developed from optical information from individuals having a known disease state. At least one factor in the algorithm is dependent on or a function of the measurement of the at least one wavelength or group of wavelengths indicative of glycosylated collagen content in tissue from the optical information of individuals forming the database.

27 Claims, 7 Drawing Sheets

U.S. PATENT DOCUMENTS

| | | |
|---|---|---|
| 5,015,100 A | 5/1991 | Doyle |
| 5,028,787 A | 7/1991 | Rosenthal et al. |
| 5,068,536 A | 11/1991 | Rosenthal |
| 5,070,874 A * | 12/1991 | Barnes et al. ............... 600/316 |
| 5,109,465 A | 4/1992 | Klopotek |
| 5,146,091 A * | 9/1992 | Knudson ................... 600/310 |
| 5,158,082 A | 10/1992 | Jones |
| 5,178,142 A | 1/1993 | Harjunmaa et al. |
| 5,188,108 A | 2/1993 | Secker |
| 5,204,532 A | 4/1993 | Rosenthal |
| 5,222,496 A | 6/1993 | Clarke et al. |
| 5,223,715 A | 6/1993 | Taylor |
| 5,224,478 A | 7/1993 | Sakai et al. |
| 5,225,678 A | 7/1993 | Messerschmidt |
| 5,237,178 A | 8/1993 | Rosenthal et al. |
| 5,243,546 A | 9/1993 | Maggard |
| 5,257,086 A | 10/1993 | Fateley et al. |
| 5,267,152 A | 11/1993 | Yang et al. |
| 5,268,749 A | 12/1993 | Weber et al. |
| 5,303,026 A | 4/1994 | Strobl et al. |
| 5,311,021 A | 5/1994 | Messerschmidt |
| 5,348,003 A | 9/1994 | Caro |
| 5,355,880 A | 10/1994 | Thomas et al. |
| 5,360,004 A | 11/1994 | Purdy et al. |
| 5,361,758 A | 11/1994 | Hall et al. |
| 5,379,764 A | 1/1995 | Barnes et al. |
| 5,402,778 A | 4/1995 | Chance |
| 5,419,321 A | 5/1995 | Evans |
| 5,435,309 A | 7/1995 | Thomas et al. |
| 5,459,317 A | 10/1995 | Small et al. |
| 5,459,677 A | 10/1995 | Kowalski et al. |
| 5,460,177 A | 10/1995 | Purdy et al. |
| 5,490,506 A | 2/1996 | Takatani et al. |
| 5,494,032 A | 2/1996 | Robinson et al. |
| 5,515,847 A | 5/1996 | Braig et al. |
| 5,533,509 A | 7/1996 | Koashi et al. |
| 5,582,168 A * | 12/1996 | Samuels et al. ............ 600/407 |
| 5,592,402 A | 1/1997 | Beebe et al. |
| 5,596,992 A | 1/1997 | Haaland et al. |
| 5,606,164 A | 2/1997 | Price et al. |
| 5,630,413 A | 5/1997 | Thomas et al. |
| 5,636,633 A | 6/1997 | Messerschmidt et al. |
| 5,655,530 A | 8/1997 | Messerschmidt |
| 5,672,875 A | 9/1997 | Block et al. |
| 5,677,762 A | 10/1997 | Ortyn et al. |
| 5,708,593 A | 1/1998 | Saby et al. |
| 5,743,262 A | 4/1998 | Lepper, Jr. et al. |
| 5,747,806 A | 5/1998 | Khalil |
| 5,750,994 A | 5/1998 | Schlager |
| 5,782,755 A | 7/1998 | Chance et al. |
| 5,792,050 A | 8/1998 | Alam et al. |
| 5,808,739 A | 9/1998 | Turner et al. |
| 5,817,007 A | 10/1998 | Fodgaard et al. |
| 5,818,048 A | 10/1998 | Sodickson et al. |
| 5,823,951 A | 10/1998 | Messerschmidt et al |
| 5,828,066 A | 10/1998 | Messerschmidt |
| 5,830,132 A | 11/1998 | Robinson |
| 5,853,370 A | 12/1998 | Chance et al. |
| 5,857,462 A | 1/1999 | Thomas et al. |
| 5,882,301 A * | 3/1999 | Yoshida ................... 600/318 |
| 5,933,792 A | 8/1999 | Andersen et al. |
| 5,935,062 A | 8/1999 | Messerschmidt et al. |
| 5,945,676 A | 8/1999 | Khalil |
| 5,957,841 A | 9/1999 | Maruo et al. |
| 6,016,435 A | 1/2000 | Maruo et al. |
| 6,025,597 A | 2/2000 | Sterling et al. |
| 6,026,314 A | 2/2000 | Amerov et al. |
| 6,034,370 A | 3/2000 | Messerschmidt |
| 6,040,578 A | 3/2000 | Malin et al. |
| 6,041,247 A | 3/2000 | Weckstrom et al. |
| 6,043,492 A | 3/2000 | Lee et al. |
| 6,045,502 A | 4/2000 | Eppstein et al. |
| 6,046,808 A | 4/2000 | Fateley |
| 6,049,727 A * | 4/2000 | Crothall ....................... 600/310 |
| 6,056,738 A | 5/2000 | Marchitto et al. |
| 6,059,724 A | 5/2000 | Campbell et al. |
| 6,061,581 A | 5/2000 | Alam et al. |
| 6,061,582 A | 5/2000 | Small et al. |
| 6,066,847 A | 5/2000 | Rosenthal |
| 6,073,037 A | 6/2000 | Alam et al. |
| 6,088,605 A | 7/2000 | Griffith et al. |
| 6,088,606 A | 7/2000 | Ignoz et al. |
| 6,110,109 A | 8/2000 | Hu et al. |
| 6,113,763 A | 9/2000 | Henry et al. |
| 6,115,673 A | 9/2000 | Malin et al. |
| 6,124,134 A | 9/2000 | Stark |
| 6,152,876 A | 11/2000 | Robinson et al. |
| 6,157,041 A | 12/2000 | Thomas et al. |
| 6,172,743 B1 | 1/2001 | Kley et al. |
| 6,192,261 B1 | 2/2001 | Gratton et al. |
| 6,212,424 B1 | 4/2001 | Robinson |
| 6,226,541 B1 | 5/2001 | Eppstein et al. |
| 6,230,034 B1 | 5/2001 | Messerschmidt et al. |
| 6,236,047 B1 | 5/2001 | Malin et al. |
| 6,240,306 B1 | 5/2001 | Rohrscheib et al. |
| 6,241,663 B1 | 6/2001 | Wu et al. |
| 6,272,367 B1 | 8/2001 | Chance |
| 6,280,381 B1 | 8/2001 | Malin et al. |
| 6,309,884 B1 | 10/2001 | Cooper et al. |
| 6,441,388 B1 | 8/2002 | Thomas et al. |
| 2002/0016534 A1* | 2/2002 | Trepagnier et al. ......... 600/316 |
| 2002/0171834 A1 | 11/2002 | Rowe et al. |
| 2003/0007147 A1 | 1/2003 | Johnson |
| 2003/0023152 A1 | 1/2003 | Abbink et al. |
| 2003/0023170 A1 | 1/2003 | Gardner et al. |

FOREIGN PATENT DOCUMENTS

| | | |
|---|---|---|
| EP | 0 426 358 A1 | 5/1991 |
| EP | 0 573 137 A2 | 12/1993 |
| EP | 0 631 137 A2 | 12/1994 |
| EP | 0 670 143 A1 | 9/1995 |
| EP | 0 681 166 A1 | 11/1995 |
| EP | 0 836 083 A1 | 4/1998 |
| EP | 0 897 691 A2 | 2/1999 |
| EP | 0 898 934 A1 | 3/1999 |
| JP | 2000-131143 | 5/2000 |
| JP | 2001-21489 | 1/2001 |
| WO | WO 86/00406 A1 | 1/1986 |
| WO | WO 92/00513 A1 | 1/1992 |
| WO | WO 92/17765 A1 | 10/1992 |
| WO | WO 93/07801 A1 | 4/1993 |
| WO | WO 97/23159 A1 | 7/1997 |
| WO | WO 97/27800 A1 | 8/1997 |
| WO | WO 98/37805 A1 | 9/1998 |
| WO | WO 98/40723 A1 | 9/1998 |
| WO | WO 99/56616 A1 | 11/1999 |
| WO | WO 00/24454 A1 | 5/2000 |
| WO | WO 00/32258 | 6/2000 |
| WO | WO 00/56207 | 9/2000 |
| WO | WO 00/65366 | 11/2000 |
| WO | WO 00/65988 A1 | 11/2000 |
| WO | WO 00/70350 | 11/2000 |
| WO | WO 01/28417 A1 | 4/2001 |
| WO | WO 01/58344 A1 | 8/2001 |
| WO | WO 01/82794 A2 | 11/2001 |
| WO | WO 01/91633 A1 | 12/2001 |
| WO | WO 01/95800 A2 | 12/2001 |
| WO | WO 02/065090 A2 | 8/2002 |

OTHER PUBLICATIONS

Atherton, P.D. et al., "Tunable Fabry-Perot Filters," *Optical Engineering*, vol. 20, No. 6, Nov./Dec. 1981, pp. 806-814.

Beebe, Kenneth R. et al., "Chapter 3: Preprocessing," *Chemometrics: A Practical Guide*, ©John Wiley & Sons, Inc., date unknown, pp. 26-55.

Brault, James W., "New Approach to High-Precision Fourier Transform Spectrometer Design," *Applied Optics*, Vo. 35, No. 16, Jun. 1, 1996, pp. 2891-2896.

Breiman, Leo, "Bagging Predictors," *Machine Learning*, vol. 24 (1996) pp. 123-140.

Cassarly, W.J. et al., "Distributed Lighting Systems: Uniform Light Delivery," *Source Unknown*, pp. 1698-1702.

de Noord, Onno E., "Multivariate Calibration Standardization," *Chemometrics and Intelligent Laboratory Systems* vol. 25, (1994) pp. 85-97.

Faber, Nicolaas, "Multivariate Sensitivity for the Interpretation of the Effect of Spectral Pretreatment Methods on Near-Infrared Calibration Model Predictions," *Analytical Chemistry*, vol. 71, No. 3, Feb. 1, 1999, pp. 557-565.

Gabriely, Ilan MD et al., "Transcutaneous Glucose Measurement Using Near-Infrared Spectroscopy During Hypoglycemia," *Diabetes Care*, vol. 22, No. 12, Dec. 1999, pp. 2026-2032.

Geladi, Paul et al., A Multivariate NIR Study of Skin Alterations in Diabetic Patients as Compared to Control Subjects, *J. Nera Infrared Spectrosc.*, vol. 8 (2000) pp. 217-227.

Haaland, David M., "Multivariate Calibration Methods Applied to the Quantitative Analysis of Infrared Spectra," *Computer-Enhanced Analytical Spectroscopy*, vol. 3 (1992), pp. 1-29.

Haaland, David M. et al. "Reagentless Near-Infrared Determination of Glucose in Whole Blood Using Multivariate Calibration," *Applied Spectroscopy*, vol. 46, No. 10 (1992) pp. 1575-1578.

Heinemann, Lutz et al., "Continuous Glucose Monitoring: An Overview of Today's Technologies and Their Clinical Applications," *IJCP Supplement 129*, Jul. 2002, pp. 75-79.

Heise H. Michael et al., "Near-Infrared Reflectance Spectroscopy for Noninvasive Monitoring of Metabolites," *Clin. Chem. Lab. Med.*, vol. 38 No. 2 (2000) pp. 137-145.

Heise, H.M. et al., "Near Infrared Spectrometric Investigation of Pulsatile Blood Flow for Non-Invasive Metabolite Monitoring," *CP430, Fourier Transform Spectroscopy: 11th International Conference*, (1998) pp. 282-285.

Heise, H.M. et al., "Noninvasive Blood Glucose Sensors Based on Near-Infrared Spectroscopy," *Artif Organs*, vol. 18, No. 6 (1994) pp. 1-9.

Heise, H.M. "Non-Invasive Monitoring of Metabolites Using Near Infrared Spectroscopy: State of the Art," *Horm. Metab. Res.*, vol. 28 (1996) pp. 527-534.

Hopkins, George W. et al., "In-vivo NIR Diffuse-reflectance Tissue Spectroscopy of Human Subjects," *SPIE*, vol. 3597, Jan. 1999, pp. 632-641.

Jagemann, Kay-Uwe et al. "Application of Near-Infrared Spectroscopy for Non-Invasive Determination of Blood/Tissue Glucose Using Neural Networks," *Zeitschrift für Physikalische Chemie*, Bd.191, S. 179-190 (1995).

Khalil, Omar S., "Spectroscopic and Clinical Aspects of Noninvasive Glucose Measurements," *Clinical Chemistry*, 45:2 (1999) pp. 165-177.

Kohl, Matthias et al., "The Influence of Glucose Concentration Upon the Transport of Light in Tissue-simulating Phantoms," *Phys. Med. Biol.*, vol. 40 (1995) pp. 1267-1287.

Kumar, G. et al., "Optimal Probe Geometry for Near-Infrared Spectroscopy of Biological Tissue," *Applied Optics*, vol. 36, No. 10, Apr. 1, 1997. pp. 2286-2293.

Kuwa, Katsuhiko et al., "Relationships of Glucose Concentrations in Capillary Whole Blood, Venous Whole Blood and Venous Plasma," *Clinica Chimica Acta*, 307 (3001) pp. 187-192.

Lorber, Avraham et al., "Local Centering in Multivariate Calibration," *Journal of Chemometrics*, vol. 10 (1996) pp. 215-220.

Lorber, Avraham et al., "Net Analyte Signal Calculation in Multivariate Calibration," *Analytical Chemistry*, vol. 69, No. 8, Apr. 15, 1997, pp. 1620-1626.

Malin, Stephen F., "Non-Invasive Measurement of Glucose by Near Infrared Diffuse Reflectance Spectroscopy," *31st Annual Oak Ridge Conference*, Sigma Diagnostics, Inc., Apr. 23, 1999, 1 sheet.

Marbach, Ralf, "Measurements Techniques for IR Spectroscopic Blood Glucose Determination," Mar. 28, 1994, pp. 1-158.

Marbach, R. et al. "Noninvasive Blood Glucose Assay by Near-Infrared Diffuse Reflectance Spectroscopy of the Human Inner Lip," *Applied Spectroscopy*, vol. 47, No. 7 (1993) pp. 875-881.

Marbach, R. et al. "Optical Diffuse Reflectance Accessory for Measurements of Skin Tissue by Near-Infrared Spectroscopy," *Applied Optics*, vol. 34, No. 4, Feb. 1, 1995, pp. 610-621.

McGarraugh, Geoff et al., "Glucose Measurements Using Blood Extracted from the Forearm and the Finger," ©TheraSense, Inc. (2001) pp. 1-7.

McGuire E.A.H. et al., "Effects of Arterial Versus Venous Sampling on Analysis of Glucose Kinetics in Man," *Journal of Applied Physiology*, vol. 41, No. 4, Oct. 1976, pp. 565-572.

Robinson, M. Ries et al., "Noninvasive Glucose Monitoring in Diabetic Patients: A Preliminary Evaluation," *Clinical Chemistry*, vol. 38, No. 9 (1992) pp. 1618-1622.

Royston, David D. et al., "Optical Properties of Scattering and Absorbing Materials Used in the Development of Optical Phantoms at 1064 NM," *Journal of Biomedical Optics*, vol. 1, No. 1, Jan. 1996, pp. 110-116.

Service, F. John et al., "Dermal Interstitial Glucose as an Indicator of Ambient Glycemia", *Diabetes Care*, vol. 20, No. 9, Sep. 1997, 9 pages.

Teijido, J.M. et al., "Design of a Non-conventional Illumination System Using a Scattering Light Pipe," *SPIE*, vol. 2774 (1996) pp. 747-756.

Teijido, J.M. et al., "Illumination Light Pipe Using Micro-Optics as Diffuser," *SPIE*, vol. 2951 (1996) pp. 146-155.

Thomas, Edward V. et al., "Development of Robust Multivariate Calibration Models," *Technometrics*, vol. 42, No. 2, May 2000, pp. 168-177.

Ward, Kenneth J. et al., "Post-Prandial Blood Glucose Determination by Quantitative Mid-Infrared Spectroscopy," *Applied Spectroscopy*, vol. 46, No. 6 (1992) pp. 959-965.

Whitehead, L.A. et al., "High-efficiency Prism Light Guides with Confocal Parabolic Cross Sections," *Applied Optics*, vol. 37, No. 22 Aug. 1, 1998, pp. 5227-5233.

* cited by examiner

APPARATUS AND METHOD FOR SPECTROSCOPIC ANALYSIS OF TISSUE TO DETECT DIABETES IN AN INDIVIDUAL

RELATED APPLICATIONS

This application is related to U.S. patent application Ser. No. 09/832,585, entitled "System for Non-Invasive Measurement of Glucose in Humans"; U.S. patent application Ser. No. 09/832,586, entitled "Illumination Device and Method for Spectroscopic Analysis"; U.S. patent application Ser. No. 09/832,631, entitled "Encoded Variable Filter Spectrometer"; and U.S. patent application Ser. No. 09/832,608, entitled "Optically Similar References Samples and Related Methods for Multivariate Calibration Models Used in Optical Spectroscopy", all filed on Apr. 11, 2001, and assigned to the assignee of the present application. Each of these related applications is hereby incorporated by reference.

FIELD OF THE INVENTION

The present invention generally relates to the field of diagnostic spectroscopy. More specifically, the present invention provides a method and apparatus for non-invasive rapid screening or diagnosis of diabetes in an individual by irradiating tissue with light comprising at least one wavelength greater than 500 nm and less than 3300 nm, collecting and measuring optical information from the tissue and applying multivariate techniques to the optical information to predict the probability of a subject having diabetes.

BACKGROUND OF THE INVENTION

In 1997, it was estimated that 15.7 million people in the United States had diabetes, of which about 10.3 million were diagnosed and 5.4 million were undiagnosed. Due to the American lifestyle of poor diet and being overweight, the incidence of diabetes is becoming of epidemic proportions. Type II diabetes accounts for 90 to 95% of all cases of diabetes in the Untied States, making it and its attendant clinical and economic consequences a major public health problem. While the prevalence of diabetes in the Unites States is about 5% of the population, care for diabetes accounts for about 15% of health care expenses.

The chronic hyperglycemia of diabetes is associated with long-term damage, dysfunction, and failure of various organs, especially the eyes, kidneys, nerves, heart, and blood vessels. Most cases of type I diabetes are detected soon after symptoms develop, which is not the case for type II diabetes. Individuals with undiagnosed type II diabetes are at significantly higher risk for coronary heart disease, stroke, and peripheral vascular disease than the non-diabetic population. They also have a greater likelihood of having dyslipidemia, hypertension, and obesity. Early detection can reduce the burden of type II diabetes and its complications as well as lessen the economic consequences.

Testing for diabetes can generally be divided into two categories, diagnostic testing and screening. "Indicating diabetes" is used herein to refer to either, or both, of these. When an individual exhibits symptoms or signs of the disease, diagnostic tests are performed and such tests confirm whether the disease is present. The purpose of screening is to identify a generally asymptomatic individual who is at high risk to develop the disease or is in the very early stages of the disease when symptoms are difficult to identify. Two screening devices have been developed for diabetes, both of which are questionnaires based on risk factors for diabetes.

In 1993, the ADA disseminated a questionnaire titled "Take the Test. Know the Score". This questionnaire assessed both possible symptoms and historical risk factors. Points were given for certain responses; a score of less than or equal to 5 points was considered low risk for diabetes, and a score of greater than 5 points was considered high risk. Subsequent testing among both United States and United Kingdom populations found that the test performed rather poorly. Two years later, another questionnaire was developed in the United States with data from the Second National Health and Nutritional Examination Survey. A test of the questionnaire in the population from which it was developed found a sensitivity of 79% (i.e., 79% of the diabetics were identified as diabetics), a specificity of 65% (i.e., 35% of the non-diabetics were identified as diabetics), and a PPV (positive predictive value) of 10% (i.e., a positive indication from the screen means the subject has a 10% chance of actually having diabetes).

Another questionnaire, developed in the Netherlands' Hoorn Study population, incorporated possible symptoms, demographic and clinical characteristics, and exercise preferences. When it was subsequently evaluated in a separate subgroup of the Hoorn Study population, this questionnaire was found to have a sensitivity of 56%, a specificity of 72%, and a performance slightly better than the ADA questionnaire for this population.

In summary, diabetes screening questionnaires, even with attempts to identify symptoms, perform rather poorly as stand-alone screening tests. Further, they are evidence of the need for an accurate screening test to identify those at high risk of developing diabetes or those in the early stages of diabetes prior to development of symptoms present at a later disease state.

In contrast to the screening questionnaires, two types of tests are currently acceptable diagnostic devices for diabetes. The fasting plasma glucose (FPG) test requires no consumption of food or beverage other than water for eight hours prior to testing. An intravenous sample of blood is drawn and tested. If the FPG test yields a glucose level in excess of 126 mg/dl, the test must be repeated at a later date. If both FPG glucose values are in excess of 126 mg/dl, the patient is diagnosed as having diabetes. The oral glucose tolerance test (OGTT) consists of a 75 g oral glucose challenge. A two-hour post load sample of blood with a value of 200 mg/dl or higher is also an indication for re-testing. While the OGTT is the more accurate of the two, the FPG is less demanding of the subject's time and is usually recommended for its convenience rather than for its accuracy.

The ADA recommends using invasive tests based on blood which are used for the diagnosis of diabetes to be also used as screening devices. The criteria is if a fasting plasma glucose (FPG) test yields a value of 126 mg/dl or higher; or if a casual plasma glucose test yields a value of 200 mg/dl or higher; or if a 75-g OGTT yields a value of 200 mg/dl or higher 2 hours later, the patient is a candidate for diagnosis of diabetes. If on a second day, one of the criteria is met a second time, then a diagnosis of diabetes is justified. It is, however, believed that these tests do not provide screening capability, as they are unlikely to identify those at risk of developing diabetes or those in the early stages of the disease.

Another set of diabetes-related tests are known which are not utilized for screening or diagnosis, but rather as a measure of the patient's long-term compliance with the therapeutic program and the patient's control of the disease. These tests are based on glycosylated proteins. Glucose will attach in a covalent bond to proteins at a rate proportional to the glucose level. This process is irreversible so the protein will remain glycosylated for the rest of its life. The accumulation of glycosylated proteins is dependent on the average life of the protein. Fructosamine is the product of glycosylated serum proteins which have a normal turn-over rate of two to three weeks. Hence, fructosamine is a marker of glucose control over the previous month. While there are some commonly available test instruments for fructosamine, they are not commonly accepted by diabetologists due to the short time window. Glycosylated hemoglobin (HbA1c) is the result of glycosylation of red blood cells which have a normal turn-over of eight to ten weeks. Hence, HbA1c is a marker for glucose control for the previous two to three months. One other glycosylation process that has been noted is glycosylated collagen (furosine). Glycosylated collagen has a very long life and a slow turn-over. As much as a thirteen-fold increase in glycosylated collagen has been found in some diagnosed diabetic patients.

The concept of using multivariate methods to classify elements into their parent populations was first put forward by Fisher in 1936. With the emergence of the computer in the 1960s, a number of authors proposed using different techniques for the computer diagnosis of disease. The techniques proposed included linear discriminant analysis (LDA), quadratic discriminant analysis (QDA) and logistic regression (LR). The diagnosis of diabetes using multivariate techniques was proposed by Gleser in 1972 where it was recommended to combine the OGTT results with other environmental factors such as age, sex, weight, etc.

Geladi et al. conducted a study that looked at using multivariate near-infrared (NIR) spectroscopic measurements with diabetics and non-diabetics. The article discussed the consequences of the changes in the microarteries and the resultant decreased blood flow resulting in tissue edema. The article discusses the use of Multi-frequency Bioelectric Impedance Analysis as well as near-infrared spectroscopy to detect the skin damage. The authors note a difference in the spectra between diabetics and nondiabetics, relating the differences to damage of the microarteries.

SUMMARY OF THE INVENTION

The present invention includes methods and apparatus for determining the probability, progression or level of diabetes in an individual. The method can be utilized to detect diabetes, whether for screening or diagnosis, in an individual. The invention can be utilized to detect type II diabetes before it is clinically identifiable through other methods currently in use such as the oral glucose tolerance test or the fasting plasma glucose test.

The method, in preferred embodiments, uses near-infrared spectroscopy to non-invasively interrogate the tissue of the subject to detect the presence, probability or progression of diabetes in an individual. Methods and apparatus of the present invention include the in vivo use of near-infrared spectroscopy in the region of 20,000 to 3000 cm$^{-1}$ (500 to 3300 nm) to do any of detect, screen, diagnose, and stage the progression of complications or predict a probability of type II diabetes in an individual. The optical information can be used to generate a predictor of disease using multivariate techniques such as discriminant analysis, quadratic discriminant analysis, logistic regression, neural nets or partial least squares. A basis of discrimination in the methods disclosed herein is based at least in part on detecting glycosylated collagen (furosine) in the tissue being tested.

Thus, the light utilized can include at least one wavelength indicative of glycosylation end products which is evidenced at least in part by glycosylated collagen content in the tissue. Further, the resulting analyzed optical information or spectral data can also include information or a measurement of light from the at least one wavelength indicative of glycosylation end products, evidenced by glycosylated collagen content in the tissue. In one embodiment, the at least one wavelength indicative of glycosylated collagen content includes a wavelength selected from the following bands: 2240 nm–2300 nm, 2145 nm–2200 nm, 2025 nm–2060 nm, and 1670 nm–1745 nm.

In another embodiment of the present invention, the light source and the resulting tissue optical information or spectral data include at least a second wavelength and wavelength information or measurement indicative of glycosylated collagen content in the tissue. Again, this second wavelength can be selected from the bands set forth above.

In a first method for detecting diabetes in an individual, tissue optical information or spectral data from the individual are obtained. The tissue optical information or spectral data includes wavelengths so that there is a differential attenuation of at least some intensities of the wavelengths, the wavelength-dependent differentiation being functions of glycosylation end products which include glycosylated proteins such as glycosylated collagen. A multivariate algorithm is developed from a database of optical information or spectral data from individuals having a known disease state. The multivariate algorithm utilizes attenuation of intensities, the attenuation being a function of the glycosylation end products. The multivariate algorithm is applied to the optical information or spectral data from the individual to detect diabetes. The present invention can also include variations on the above method for non-invasively detecting diabetes using spectroscopic measurements of human tissue.

In this embodiment, an illumination source is provided and used to irradiate tissue with light having at least one wavelength indicative of glycosylation end products as evidenced by glycosylated collagen content in the irradiated tissue. At least a portion of the light exiting the irradiated tissue is collected and the intensity of this light at selected wavelengths is measured. Multivariate techniques are then applied to the measured intensity to predict the probability of the subject having diabetes mellitus. The multivariate techniques include as a factor the differential attenuation of at least one wavelength or group of wavelengths indicative of glycosylation end products such as glycosylated collagen content in the tissue.

An apparatus for conducting the methods of the present invention includes a light source that generates light, including light at at least one wavelength indicative of glycosylation end products as evidenced by glycosylated collagen content in tissue. The apparatus further includes a sampling means for coupling the light to tissue and collecting at least a portion of the light modified by the tissue. A spectrometer is coupled to the sampling means for measuring the spectra of the modified light collected from the tissue. Means for processing the measured spectra to determine the probability, progression or level of diabetes are also included. The means for processing the measured spectra includes an algorithm having as at least one factor the measurement of light at the at least one wavelength indicative of glycosylation end products as evidenced by glycosylated collagen content in the tissue.

In a further embodiment of the apparatus of the present invention, the system includes a tissue sampling subsystem optically coupled to an illumination subsystem. The illumination subsystem generates near-infrared light, including at least one wavelength indicative of glycosylation end products as evidenced by glycosylated collagen content in human tissue. The tissue sampling subsystem receives at least a portion of the infrared light. The tissue sampling subsystem includes a means for irradiating the human tissue with at least a portion of the received near-infrared light and also collecting at least a portion of the light diffusely reflected from the human tissue.

A system can further include an FTIR spectrometer subsystem optically coupled to the tissue sampling subsystem to receive at least a portion of the light diffusely reflected from the tissue, with the FTIR spectrometer subsystem including a spectrometer that creates an interferogram and a detector which receives the interferogram and converts it to an electrical representation. The system further can include a data acquisition subsystem which receives the electrical representation of the interferogram and includes means for amplifying and filtering the electrical representation and converting the resulting electrical signal to its digital representation. The system can also include a computing subsystem for receiving the digital representation which further includes a calibration model derived from a multivariate analysis for detecting the probability, progression or level of diabetes wherein the calibration model includes at least one factor dependent on measurement of the at least one wavelength indicative of glycosylation end products as evidenced by glycosylated collagen content in human tissue. The algorithm can be used to classify the individual as diabetic or non-diabetic.

DETAILED DESCRIPTION OF THE INVENTION

Figure 1:
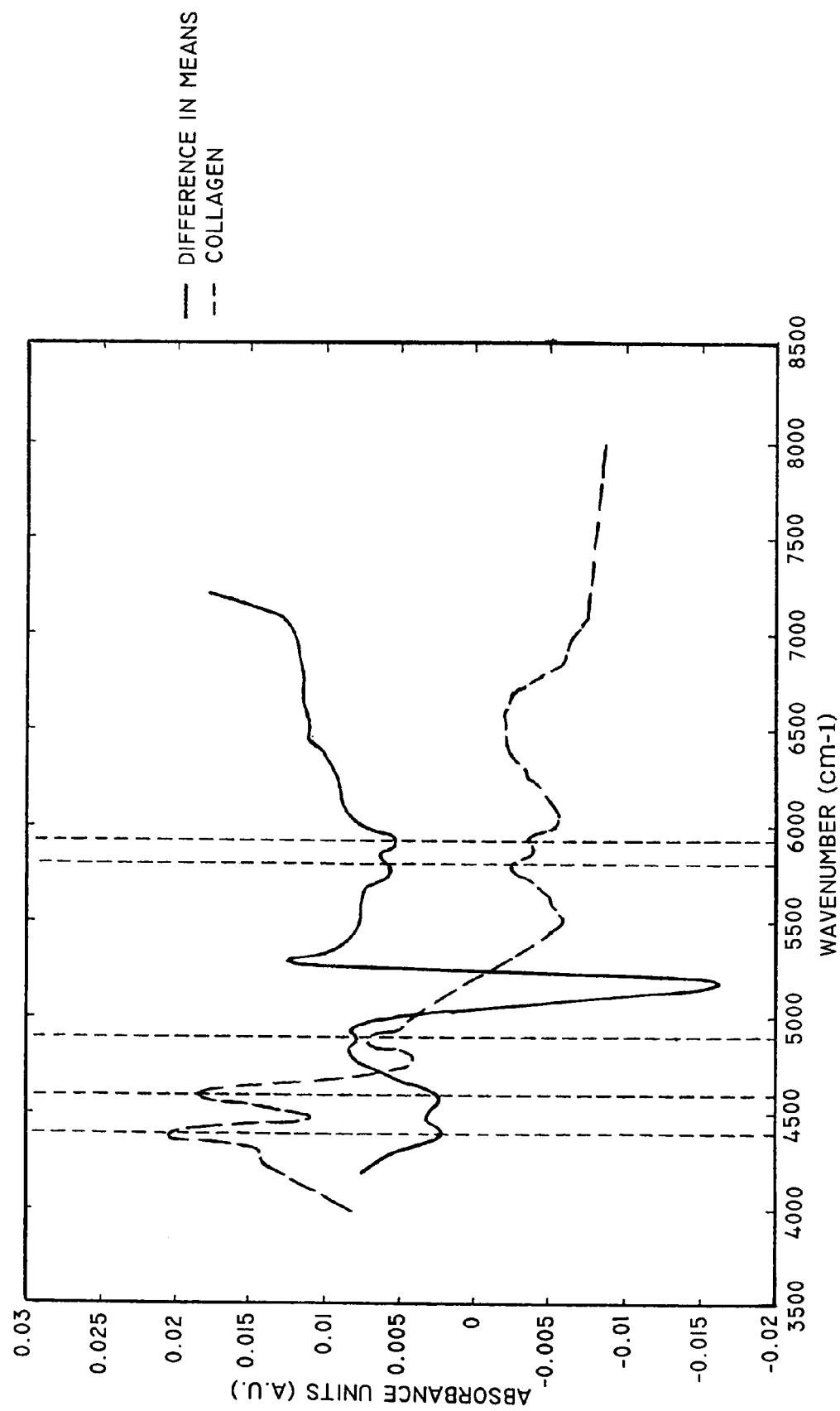
FIG. 1 is a plot depicting the difference in mean spectra of a sample population of diabetic and non-diabetic individuals compared with the spectrum of collagen.

The following detailed description should be read with reference to the drawings in which similar elements in different drawings are numbered the same. The drawings, which are not necessarily to scale, depict illustrative embodiments that are not intended to limit the scope of the invention.

Embodiments of the present invention include apparatus and methods useful for providing rapid, accurate diagnosis of diabetes without the incumbent drawbacks of the present fasting plasma glucose test or the oral glucose tolerance test. The methods and apparatus can also be used for screening diabetes, including type II diabetes, before it is clinically identifiable through other methods currently in use. The method can use near-infrared spectroscopy to non-invasively interrogate the tissue of the subject to detect the presence or progression of diabetes.

The method, in one embodiment, includes the in vivo use of optical spectroscopy with wavenumbers in the region of 20,000 to 3000 $cm^{-1}$ (wavelengths in the region of 500 to 3300 nm) to screen or diagnose type II diabetes mellitus. The optical information which may be processed in the form of spectra can be used to generate a predictor of disease using multivariate methods such as linear discriminant analysis, quadratic discriminant analysis, logistic regression, neural nets, and partial least squares regression. The method of discrimination is based in part on detecting evidence of elevated glucose as seen by the level of glycosylation end products preferably evidenced by glycosylated collagen (furosine) in the tissue analyzed.

Individuals who have been diagnosed with diabetes have an elevated level of glycosylated collagen and glycosylated collagen levels can be utilized as a distinct marker of long-term glucose control. Applicants have found that near-infrared spectroscopic techniques can be utilized with multivariate techniques to provide both screening and diagnosis of diabetes based on changes in the tissue associated with increasing levels of glycosylation end products such as glycosylated collagen. It is possible that, as collagen glycosylates, it unravels and cross-links which causes an increased level of scatter for light. The increased level of scatter results in more light returned, or in other words, less absorption of light. Also, glycosylated collagen directly absorbs light around several characteristic wavelengths. In the present invention, tissue can be irradiated with light having at least one wavelength that is indicative of glycosylated collagen content in the tissue (by increased scatter or by increased direct absorption). Multiple or groups of wavelengths of light which are indicative of level of glycosylated collagen are utilized. Suitable wavelengths include, but are not limited to, wavelengths selected the following bands: 2240 nm–2300 nm, 2145 nm–2200 nm, 2025 nm–2060 nm, and 1670 nm–1745 nm.

Applicants have found that the detection or screening of diabetes utilizing near-infrared spectroscopy is facilitated by measuring the optical information or spectrum of an individual's tissue and looking at identified peaks for the presence of elevated levels of glycosylation end products at multiple wavelengths. Thus, in an embodiment for diagnosing or screening diabetes, data comprising near-infrared optical information or spectra and blood glucose readings from non-diabetics, subjects with impaired glucose tolerance and newly diagnosed type II diabetics is utilized in the multivariate analysis. The optical information or spectra used can correspond to concurrent blood glucose levels less than some maximum level, for example 125 mg./dl, to prevent transient glucose levels from being the predictor for disease state. Other methods can be utilized to delimit the effect of blood glucose level in a particular individual. A fasting glucose tolerance test and an oral glucose tolerance test can also be administered to the subjects to confirm their membership in one of the three above classes. The data can include a sufficient number of subjects in each of the three categories to develop a calibration so that the discrimination algorithms developed utilizing this database create predictors that give proper determination of the disease state of the individual. Further, optical information and spectra are terms used throughout this disclosure. However, it is recognized that measuring a spectrum is only one of many ways to encode optical information for analysis. In preferred embodiments, spectral data is utilized.

For calibration development, a database can be utilized including near-infrared spectra, fasting glucose tolerance tests and oral glucose tolerance test results for at least 3000 believed non-diabetics. A fasting oral glucose tolerance test and an oral glucose tolerance test can be administered to each participant to determine that subject's true disease state. Given the incidence of undiagnosed diabetes in the United States, it is believed that a sufficient sample of approximately 75 undiagnosed type II diabetics would be identified in the database by the glucose tolerance tests employed. The undiagnosed diabetic can be a preferred subject as the extent of glycosylation of collagen can be more typical for screening than for one who had already been diagnosed and is under some treatment for diabetes. This method allows an accurate calibration to be established which helps in accurate classification of newly tested individuals. It also provides the basis for screening those patients at high risk for developing diabetes or having diabetes, but not yet experiencing readily identifiable symptoms as compared to those having been diagnosed earlier with diabetes.

A suitable database can also include the use of non-diabetics in an at-risk population. One such population can include subjects who are seriously overweight or close relatives of patients with type II diabetes. Another such population can include non-diabetics from certain ethnic groups with very high propensities for type II diabetes such as the Pima Indians. Again, the oral glucose tolerance tests can be used on all subjects to determine their particular disease state.

The ability of near-infrared spectroscopy to measure an individual's tissue and the use of multivariate analysis on a database of individuals to classify the test individual based on glycosylated collagen can be illustrated by examining and understanding the progression of glycosylation end products with the advance of type II diabetes. For example, in pre-diabetic subjects there is an apparent mismatch between the initial insulin response to a carbohydrate load and the glucose production resulting from that load. This mismatch results in a prolonged post-prandial rise of glucose. The production of glycosylated end products is believed proportional to the average glucose level and duration of increased glucose levels. This results in an increased rate of glycosylation and an increased accumulation of glycosylation end products as evidenced by increased accumulation of such materials as glycosylated collagen. The accumulation is believed amplified by the extreme persistence of collagen. As a result, the glycosylated collagen is an early marker for the excessive elevated post-prandial excursions in pre and early diabetic patients. As the diabetes progresses to the state of frank diabetes, the glucose level is permanently elevated. If the patient receives medical care to control the glucose levels, the rate of glycosylation reaches an equilibrium state. Consequently, the most rapid rise in the glycosylation of collagen is believed to occur early in the progression of diabetes. This is exactly the condition when screening or diagnosis is most desirable and effective in the long-term management of the disease. Due to the long lifetime of collagen, the accumulation of glycosylated collagen is rapid in the early stage before any type of equilibrium is reached. This makes glycosylated collagen a sensitive marker for monitoring the early progression of diabetes mellitus. Further, the long lifetime of collagen makes glycosylated collagen a marker of long-term control and it is a marker of diabetic complications which make it useful to diagnose the stage of the disease.

To show the ability to diagnose type II diabetes with near-infrared spectroscopy combined with multivariate analysis, utilizing the method and apparatus of the present invention, an experimental data set was developed using 18 type II diabetics with good glucose control and 20 non-diabetics. The diabetics covered a range from 1 year since diagnosis to 10 years. The optical responses of their tissue were collected using a Fourier transform infrared (FTIR) spectrometer and system as described in herein. The measurements were made on the underside of the forearm. A total of 913 near-infrared spectra were used with 461 of the near-infrared spectra being from type II diabetics, and 452 spectra from non-diabetics. Corresponding blood glucose measurements were made using capillary blood measured with a Yellow Springs Instruments, Inc. blood analyzer. Only near-infrared measurements that corresponded to a blood glucose level less than or equal to 125 mg/dl were used in order to prevent the glucose level being the delineating element in the comparison between type II diabetics and non-diabetics. The spectra collected were screened for poor insertion of the forearm onto the tissue sampler of the invention. The spectra were also scaled with the mean intensity spectrum to make the noise more homogeneous over the wavenumber range.

The difference in mean spectra between type II diabetics and non-diabetics is compared with the spectrum for collagen in FIG. 1. As can be seen, the collagen peaks at 1690 nm, 1725 nm, 2040 nm, 2170 nm or 2270 nm (4400, 4600, 4900, 5800 and 5925 cm$^{-1}$) are repeated in the difference spectra of type II diabetics and non-diabetics. An increased absorption in the prevalent water region about 1425 nm (7000 cm$^{-1}$) can be observed. It should be noted that while the 1920 nm (5200 cm$^{-1}$) water band has similar information, the absorbance in that band is so great as to give a very low signal-to-noise ratio.

Figure 2:
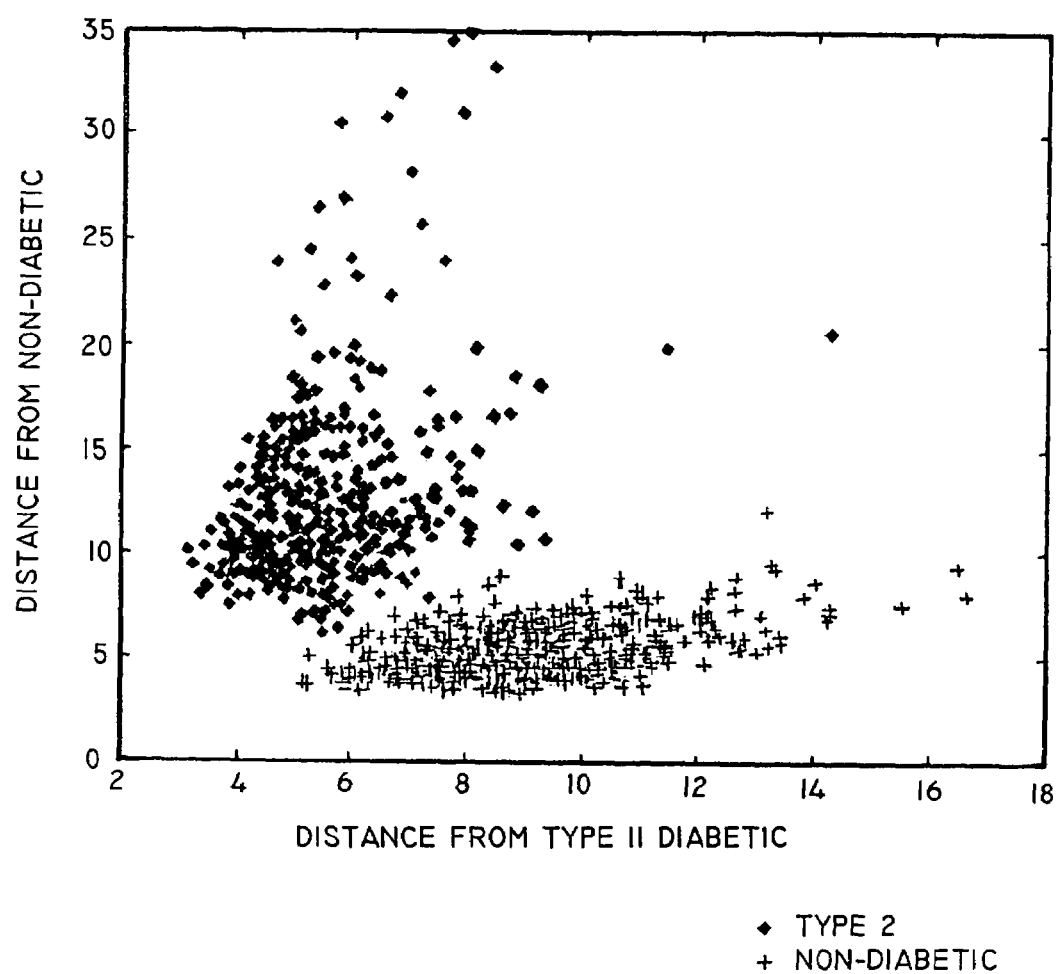
FIG. 2 is a plot depicting discriminant distance between diabetics and nondiabetics in a set of collected spectral data.
Figure 3:
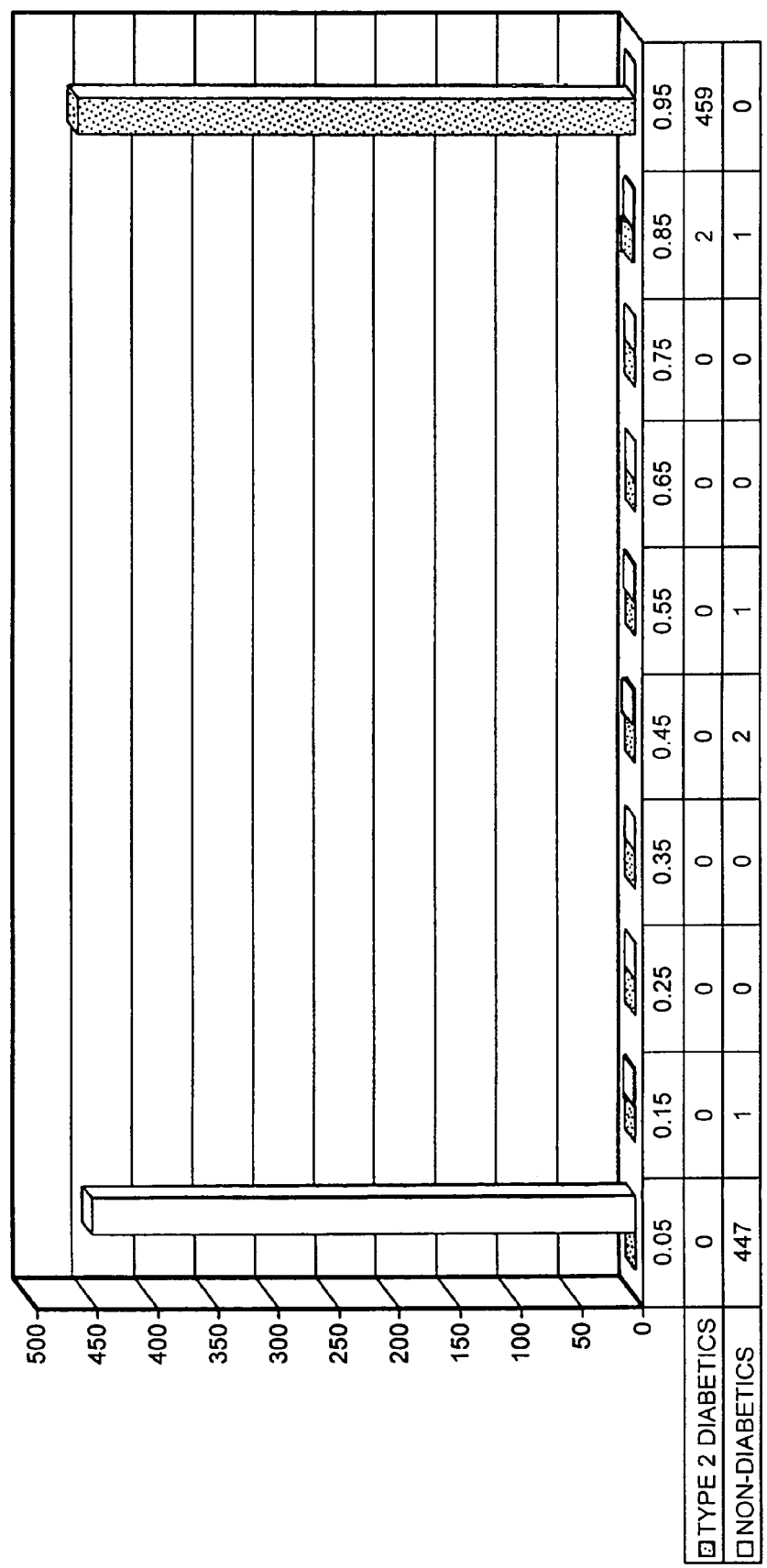
FIG. 3 is a plot depicting Mahalanobis distance for the data of FIG. 2.

The data analysis shows an ability to distinguish between the disease state of type II diabetics and non-diabetics. FIG. 2 shows the separation for the two groups from the diseased and non-diseased population. A very clear distinction of groups is seen. Further, a Bayesian discriminant function was used to discriminate type II diabetics from non-diabetics. Using the information that approximately 10% of the adult U.S. population has type II diabetes, the Bayesian discriminant function produces the posterior probabilities for the subjects from the two groups to be non-diabetic as shown in FIG. 3. The Mahalanobis distance analysis yields a sensitivity of the instrument of 100%, a selectivity of 98.9% and a positive predictive value of 98.9%. It can also be calibrated on each subject to give estimates of the progression of the disease in a pre-diabetic patient as well as a marker of disease control similar to HbA1c. The Bayesian analysis can also use a prior probability based on environmental risk factors such as used by the ADA test "Take the test, know the score."

The above description shows the ability of the present invention to diagnose diabetes. The present invention's ability to screen those individuals tested who have a high risk of developing diabetes or who have diabetes in the earliest stages is a natural extension from the above model. A database can be developed which includes spectra of individuals at a time prior to being able to diagnose diabetes using the glucose tolerance tests, yet subsequently, these individuals develop diabetes. Thus, the database can be developed over time so that spectra of those in the early stages of diabetes are, in fact, confirmed to be indicative of the onset of the disease based on known analyses later in time. This can require monitoring of many individuals over an extended period of time. However, as previously discussed, building of the database can be focused on those individuals who are believed at risk for developing diabetes based on family history and other factors such as those in the screening questionnaires. Also, as previously stated, a large sample population of yet undiagnosed individuals will likely identify many individuals early in the progression of the disease. Further, the ability of the present invention to detect the early changes in glycosylated collagen is enhanced by a system for measurement of the spectroscopic data in the tissue. Embodiments of the apparatus and method are described below.

Also in an embodiment of the present invention, an algorithm can be developed to discriminate membership in the population within a database. The algorithm can use partial least squares (PLS) to reduce the dimensionality of the near-infrared spectra together with quadratic discriminant analysis since the variation of near-infrared spectra for diabetics is considerably greater than the near-infrared spectra for non-diabetics. The spectra in the database make up the rectangular matrix with the number of rows equal to the number of near-infrared spectra and the number of columns equal to the number of frequencies in the spectra. The columns of the spectral matrix are usually highly correlated; however, the discriminant analysis can work better if the matrix can be transformed to be uncorrelated. Likewise, the correlation between columns implies that fewer columns can be used once transformed. While principle component analysis (PCA) can be used to accomplish these two tasks, partial least squares (PLS) used to predict the disease state (diabetic versus non-diabetic) can accomplish the same thing while making the columns more highly correlated with the disease stage of the subject and reducing the number of factors needed in the prediction.

While linear discriminant analysis (LDA) can be used to develop a predictor of disease state, LDA assumes the covariance matrix of the spectra within each group is the same. This assumption, unfortunately, is not true as the diabetic population is far more variable in several characteristics, including their near-infrared spectra. So, the covariance matrix cannot be expected to be equal over the different disease stage groups. Quadratic discriminant analysis (QDA), on the other hand, assumes a different covariance matrix for each population. Hence, QDA can be used to develop the predictors of disease state. An offshoot of the LDA and QDA is the Bayesian classifier which predicts the probability of diabetes. Risk factors for diabetes can be incorporated into the prior probability for a Bayesian analysis. Other processing steps such as multiplicative scatter correction (MSC) and normalization are not necessarily needed to accurately discriminate near-infrared spectra as to the disease state of the subject, although they can be utilized.

An apparatus for diagnosing or screening for diabetes incorporates an illumination subsystem which generates near-infrared light, a tissue sampling accessory which irradiates and collects light from tissue, a spectrometer, a data acquisition subsystem, a reference device for calibration maintenance, a processing unit, and calibration coefficients based on certain multivariate algorithms. Each subsystem has significant impact on the accuracy of the predictions of presence of diabetes mellitus. Examples of the first six subsystems suitable for the present invention are disclosed in detail in U.S. patent application Ser. No. 09/832,585, filed on Apr. 11, 2001, and entitled "System for Non-Invasive Measurement of Glucose in Humans," incorporated herein by reference.

In one embodiment of the system, the spectral encoding is performed after light has interacted with the tissue. The light source can be an illumination device as disclosed in U.S. patent application Ser. No. 09/832,586, filed Apr. 11, 2001, entitled "Illumination Device and Method for Spectroscopic Analysis," incorporated herein by reference. Examples of light sources include tungsten filaments, QTH, glowbars or any continuous wave gray body sources. The sampler can include a blocker that separates the input light from the output light as disclosed in U.S. Pat. No. 6,230,034, entitled Diffuse Reflectance Monitoring Apparatus, and incorporated herein by reference. The spectrometer can be any device that allows the interpretation of the wavelength information from the modified light exiting the tissue interface. Such systems include Fourier transform infrared spectrometers, acousto-optical tunable filters, dispersive spectrometers utilizing a detector array, a stepped dispersive system with a single detector, and an encoded spectrometer such as a Hadamard transform device. Examples of suitable photo-detectors include photovoltaic detectors such as Si, InGaAs, InAs, Ge and InSb, photo-conductive detectors such as PbS and PbSe, and pyroelectric detectors such as DTGS and lithium tantalate.

In another embodiment of the system, the light is encoded prior to interrogating the tissue. The spectrometer can be any device that encodes the wavelength information in the light entering the tissue interface. Exemplary devices are disclosed in U.S. patent application Ser. No. 09/832,631, filed Apr. 11, 2001, entitled "Encoded Variable Filter Spectrometer," incorporated herein by reference. Such systems can include stepped dispersive spectrometers or an encoded spectrometer such as a Hadamard transform device or an FTIR. Examples of suitable photo-detectors include photovoltaic detectors such as Si, InGaAs, InAs, Ge and InSe, photo-conductive detectors such as PbS and PbSe, and pyroelectric detectors such as DTGS and lithium tantalate.

Since for many tissue test sites collagen is within 2 mm of the surface, the near-infrared light should be in a range of wave numbers that will penetrate tissue to that depth in order to interrogate the collagen containing tissue. Light having wavelengths in region from 1250 nm to 2500 nm (wavenumbers in the region from 8000 to 4000 $cm^{-1}$) is suitable for analysis according to the present invention. Some sites that contain collagen within 2 mm of the surface include the underside of the forearm, the thigh, the calf, the back of the hand and the thenar.

Figure 4:
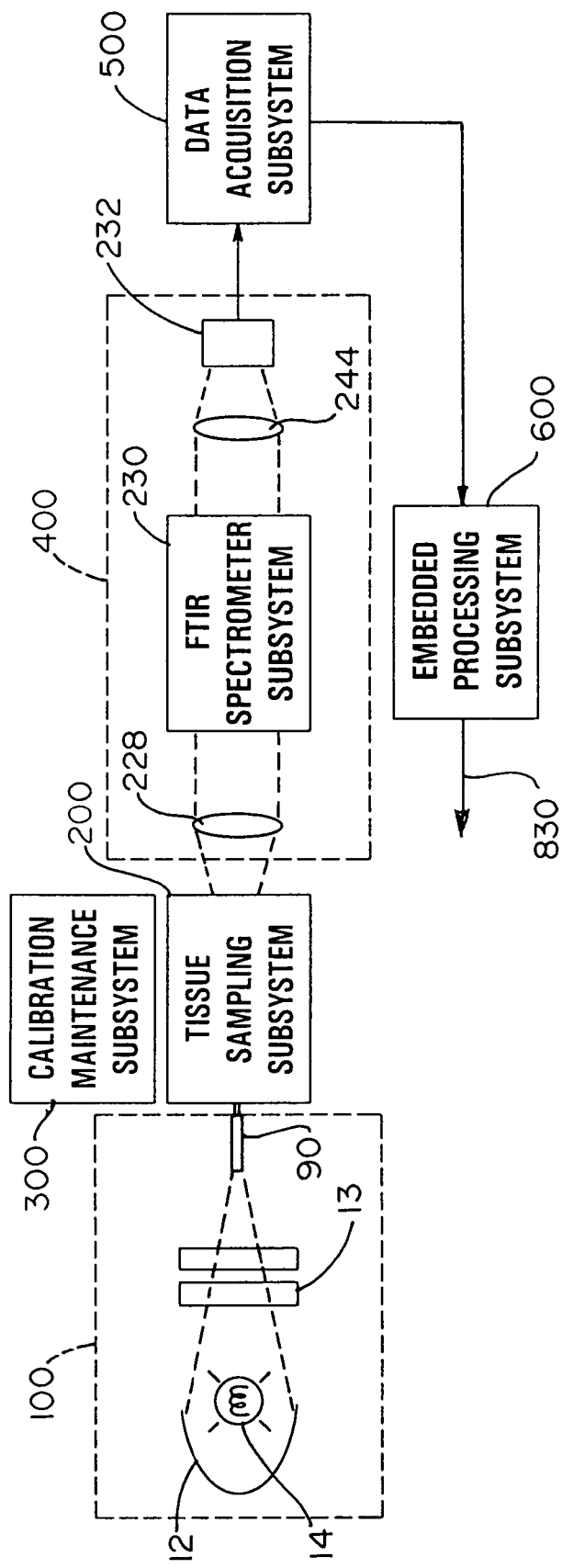
FIG. 4 is a schematic depiction of a non-invasive spectrometer system.

Referring now to FIG. 4, a system for diagnosing or screening for diabetes is depicted in schematic view. The overall system includes six subsystems. The subsystems include an illumination subsystem 100, a tissue sampling subsystem 200, a calibration maintenance subsystem 300, an FTIR spectrometer subsystem 400, a data acquisition subsystem 500 and an embedded processing subsystem 600. The subsystems can be designed and integrated in order to ensure that the signal-to-noise ratio is preserved to the maximum amount. The net analyte signal-to-noise ratio is directly related to the accuracy and precision of the non-invasive classification of individuals as diabetic or non-diabetic by near-infrared spectroscopy with the present invention.

The subsystems can provide reproducible and preferably uniform radiance of the tissue, low tissue sampling variance, depth targeting of the collagen-bearing layers of the tissue, efficient collection of diffuse reflectance spectra from the tissue, high optical throughput, high photometric accuracy, large dynamic range, excellent thermal stability, effective calibration maintenance, effective calibration transfer, built-in quality control and ease-of-use. Each of the subsystems is discussed below in detail.

The illumination subsystem 100 generates the near-infrared (NIR) light used to interrogate the tissue of a human for the non-invasive determination of disease state. The illumination subsystem, in an exemplary embodiment, contains a broadband, polychromatic light source 14 that emits radiation in the near-infrared portion of the spectrum. The light source 14 may emit radiation outside of the near-infrared, also. An example of a suitable light source 14 would be a 40-watt, 22.8-volt tungsten filament lamp. The light source 14 is typically driven by a regulated power supply. The power supply may supply the lamp with constant current, constant voltage or constant power. The power supply for the light source can provide regulation of current, voltage or power to keep the color temperature and emissivity of the light source as stable as possible. Fluctuations of the light source's color temperature and emissivity can be a source of noise in the non-invasive measurement and can reduce the net analyte signal to noise ratio (SNR) and, subsequently, the accuracy and prediction capability of the measurement.

The overall system of the present invention can include a power supply which provides regulated, low noise power to all of the subsystems. The power supply can be a 300-watt, quad output, resonant power, medical grade, AC power to DC converter that provides output voltages of +28, +15, −15, and +5 VDC. The ripple on each of the voltages can be less than 20 millivolts peak-to-peak and the switching frequency of the supply can be greater than 200 kilohertz to facilitate additional filtering of the power and to further reduce noise. Additionally, the power supply can have a conversion efficiency of at least 80% which can be important to reduce the thermal loading of the non-invasive instrument to the point that only convection cooling is required for normal device operation. The illumination subsystem 100 utilizes 28 VDC power from the power supply to drive the light source. A DC-to-DC converter can regulate the input power down to 21.4 VDC and also can provide a soft start function that gradually turns on the light source when the system is first turned on. The soft start function can extend the useful life of the light source by eliminating startup transients and limiting the current required to initially power the light source.

In addition to the light source and regulated power supply, the illumination subsystem can contain optical elements 12, 13, 90 that collect the radiation from the light source and transfer that light to the input of the tissue sampling subsystem. The elements that makeup the transfer optics can include collimating and/or condensing optics, optical filters, optical diffusers, a homogenizer or light pipe for scrambling and the corresponding mechanical components to hold the optics and light source.

The collimating optics can be refractive (e.g., a lens) or reflective (e.g., an elliptical mirror) elements. The condensing optics can also be refractive or reflective. Materials for lenses and mirrors are known in the art. The reflective optics can have a smooth finish, a rough finish or a faceted finish depending on the configuration of the illumination subsystem. A rough or faceted finish for the reflective optics can destroy the coherence of the light source image and create a more uniform radiance pattern. The refractive optics can be spherical or aspherical. A Fresnel lens is a special type of aspherical lens that also can be employed. The collimating and/or condensing optics can collect radiation from the source and transfer the radiation to the input of the tissue sampling subsystem 200 or to other optical elements that perform additional operations on the light before it is passed to the tissue sampling subsystem 200.

One or more optical filters 13 can be employed to preferentially pass radiation only in the spectral region of interest. The optical filter can be one or a combination of long pass, short pass, or band pass filters. These filters can be absorptive, interference or dichroic in nature. In some embodiments, the optical filters are anti-reflection coated to preserve the transmittance of light in the spectral region of interest. These filters can also perform spectral shaping of the radiation from the light source to emphasize certain portions of the near-infrared spectrum over others. The optical filtering can bandlimit the radiation impinging on the tissue and increase the SNR in the region of interest and to keep from burning or otherwise damaging the tissue of the subject. Bandlimiting the radiation can improve the effective SNR by reducing detector Shot noise that results from unwanted radiation outside the spectral region of interest.

The optical diffusers 13 and scramblers 90 in the illumination subsystem can provide reproducible and uniform radiance at the input of the tissue sampling subsystem 200. Uniform radiance can help ensure good photometric accuracy and even illumination of the tissue. Uniform radiance can also help reduce errors associated with manufacturing differences between light sources. Uniform radiance is utilized in the present invention for achieving accurate prediction of disease state.

An example of an optical diffuser is a ground glass plate. The ground surface of the plate effectively scrambles the angle of the radiation emanating from the light source and its transfer optics. A light pipe can be used to scramble the intensity of the radiation such that the intensity is uniform at the output of the light pipe. In addition, light pipes with a double bend can scramble the angles of the radiation. For creation of uniform intensity and angular distribution, the cross section of the light pipe should not be circular. Square, hexagonal and octagonal cross sections can be effective scrambling geometries. The output of the light pipe may directly couple to the input of the tissue sampler or may be used in conjunction with additional transfer optics before the light is sent to the tissue sampler.

Figure 5:
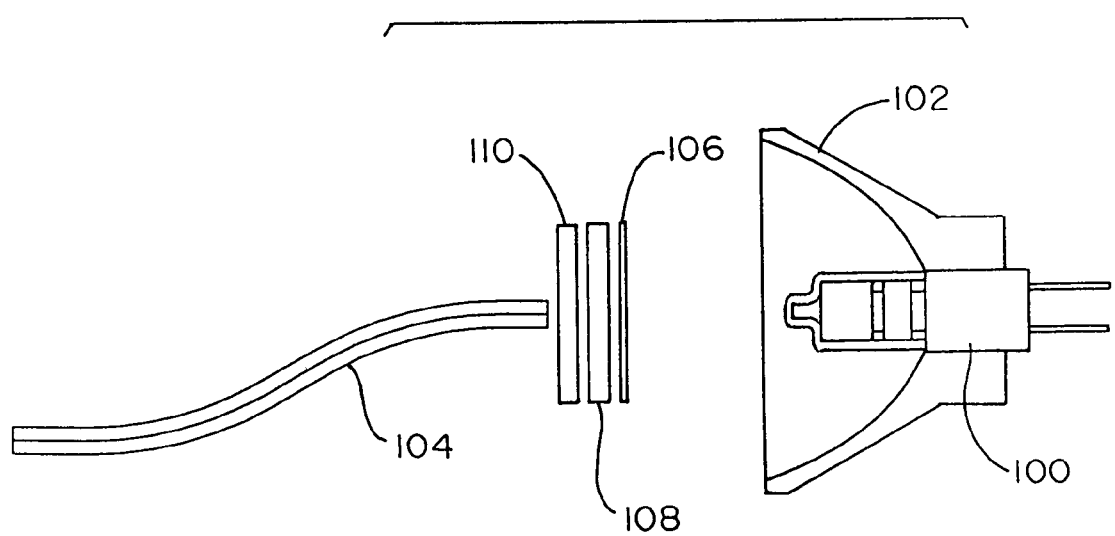
FIG. 5 is a diagrammed view of a system incorporating filters which eliminate selected wavelengths of radiation from the illumination source.

Now referring to FIG. 5, another aspect of the present invention is depicted. The system depicted provides spectral filtering or bandpass filtering to eliminate unnecessary wavelengths or bands of wavelengths from the light prior to contact with the tissue. This is accomplished by placing one or more elements between the light source and tissue. The elements can include absorptive filters fabricated of any transparent or partially transparent substrate; single layer or multi-layer dielectric coatings deposited on any transparent or partially transparent substrate; a grating or prism which disperses the radiation, permitting unwanted wavelengths to be blocked from reaching the tissue; and/or an aperture which selectively blocks undesirable radiation.

A system for bandpass filtering is depicted in FIG. 5, which depicts a light source 101 placed within an electrical reflector 102. FIG. 5 also depicts a hexagonal S-bend light pipe 104 to receive light from the source 101. A series of filters are placed between the light source 101 and the light pipe 104. The first optical filter is a silicon filter 106 which is anti-reflection coated to transmit at least ninety percent (90%) of the in band incident light. The silicon filter passes wavelengths of light longer than 1.1 micron. The second optical filter can be a KOPP 4-67 colored glass filter 108 that, in combination with the silicon filter, passes light in the 1.2 to 2.5 micron spectral region. The slope of the KOPP filter is such that it preferentially passes light at wavelengths between 2.0 and 2.5 micron. The third optical filter can be an ORIEL WG295 absorption filter 110 that cuts out wavelengths longer than 2.5 micron. The front surface of the WG295 filter can be polished or finely ground. If the front surface is finely ground, the WG295 acts as a diffuser as well as a light filter. These filters can prevent burning of the tissue, while enhancing the signal-to-noise ratio of the system by band limiting the light to only the spectral region of interest. Band limiting the light can reduce shot noise generated by the photon flux incident on the detector.

Figure 6:
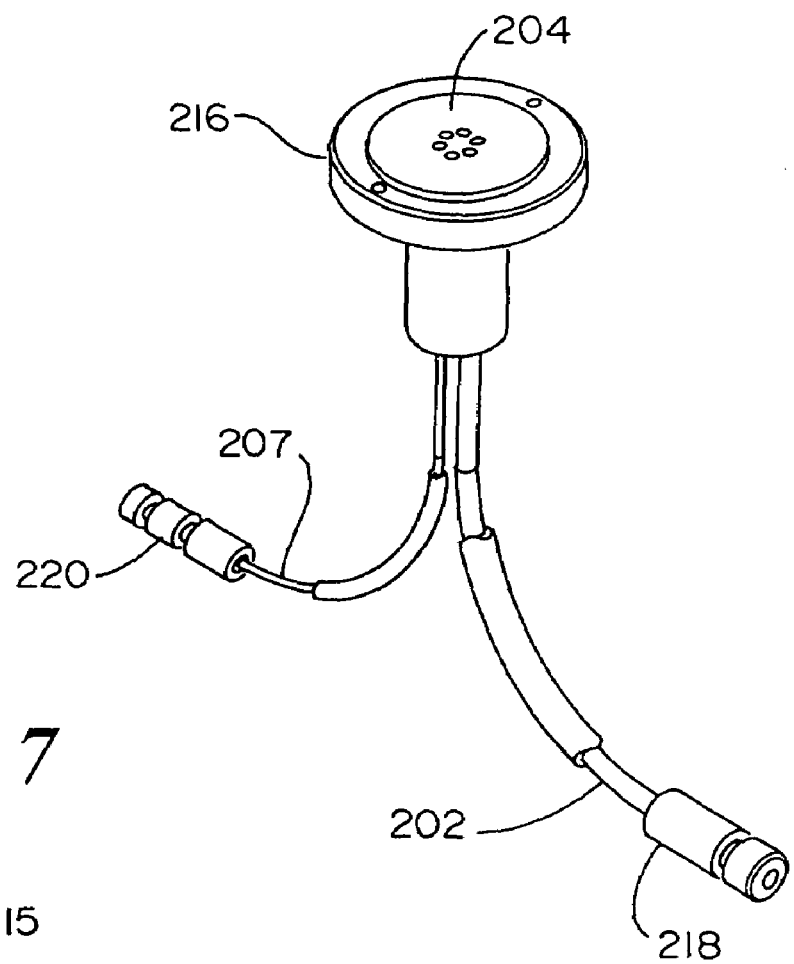
FIG. 6 is a perspective view of elements of a tissue sampling subsystem.
Figure 7:
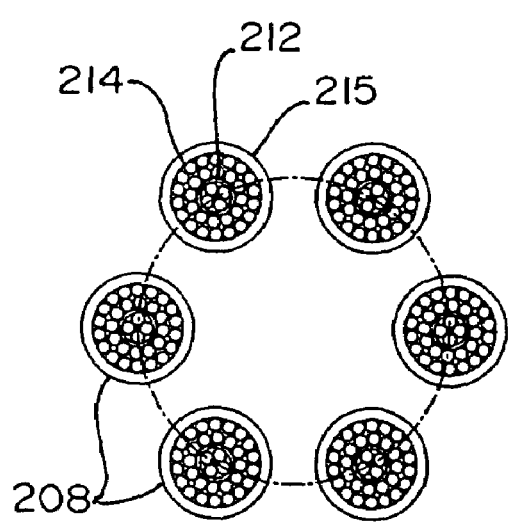
FIG. 7 is a plan view of the sampling surface of the tissue sampling subsystem of FIG. 6 showing an arrangement of input and output optical fiber ends.
Figure 8:
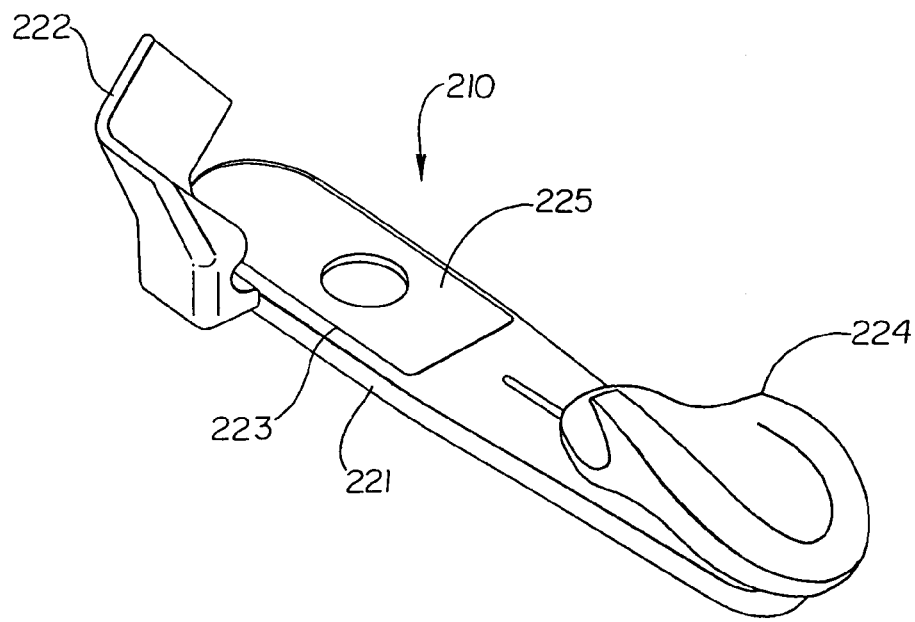
FIG. 8 is a perspective view of an ergonomic apparatus for holding the sampling surface and positioning a tissue surface thereon.

Tissue sampling subsystem 200 can to introduce radiation generated by the illumination subsystem 100 into the tissue of the subject and can collect the portions of the radiation that are not absorbed by the tissue and send that radiation to the FTIR spectrometer subsystem 400 for measurement. FIGS. 6, 7 and 8 depict elements of a tissue sampling subsystem 200. Referring first to FIG. 6, the tissue sampling subsystem 200 has an optical input 202, a sampling surface 204 which forms a tissue interface 206 that interrogates the tissue and an optical output 207. The subsystem can further include an ergonomic apparatus 210, depicted in FIG. 8, which holds the sampling surface 204 and positions the tissue at the interface 206. A device that controls the temperature of the tissue interface can be included and, in some embodiments, an apparatus which repositions the tissue on the tissue interface in a repetitive fashion is included.

The optical input 202 of the tissue sampling subsystem 200 receives radiation from the illumination subsystem 100 (i.e., light exiting the light pipe) and transfers that radiation to the tissue interface 206. The optical input can consist of a bundle of optical fibers that are arranged in a geometric pattern that collects the most light possible from the illumination subsystem. One arrangement is depicted in FIG. 7. The plan view depicts the ends of the input and output fibers in a geometry at the sampling surface including six clusters 208 arranged in a circular pattern. Each cluster includes four central output fibers 212 which collect diffusely reflected light from the tissue. Around each grouping of four central output fibers 212 is a cylinder of material 215 which ensures about a 100 μm gap between the edges of the central output fibers 212 and the inner ring of input fibers 214. The 100 μm gap can be important to target collagen in the tissue. As shown in FIG. 7, two concentric rings of input fibers 214 are arranged around the cylinder of material 215. As shown in one embodiment, 32 input fibers surround the four output fibers. The high ratio of input-to-output fibers is maintained in recognition of loss within the tissue.

All of the clustered input and output fibers can be potted into a cluster ferrule which is glued into a sampling head 216. The sampling head 216 includes the sampling surface 204 which can be polished flat to allow formation of a good tissue interface. Likewise, the input fibers can be clustered into a ferrule 218 connected at the input ends to interface with the illumination subsystem 100. The output ends of the output fibers can be clustered into a ferrule 220 for interface with the FTIR spectrometer subsystem 400.

Alternatively, the optical input can use a combination of light pipes, refractive and/or reflective optics to transfer the maximum amount of input light to the tissue interface. The input optics of the tissue sampling subsystem can collect as much light as possible from the illumination subsystem 100 in order to maximize the SNR achieved by the overall system. In the present invention, the placement of the illumination subsystem 100 and tissue sampling subsystem 200 before the FTIR spectrometer subsystem 400 can result in over an order of magnitude improvement in throughput for a given size of FTIR spectrometer because the input to the tissue sampling subsystem 200 is designed to handle the wide range of angles from the illumination subsystem 100 and the small output image size of the tissue sampling subsystem is better matched to the throughput supported by a reasonably sized FTIR spectrometer. The benefits of source, sample, FTIR spectrometer, detector (SSFD) configuration for non-invasive classification of disease state can be significant.

The tissue interface can irradiate the tissue in a manner that targets the collagen bearing portions of the tissue and discriminate against light that does not travel a significant distance through those portions. As stated above, the 100 μm gap discriminates against light which contains little useful information. In addition, the tissue interface can average over a certain area of the tissue to reduce errors due to the heterogeneous nature of the tissue. The tissue sampling interface can reject specular (returned by specular reflection from the tissue surface) and short pathlength rays and it can collect the portion of the light that travels the desired pathlength through the tissue with high efficiency in order to maximize the SNR of the system. The tissue sampling interface can employ optical fibers to channel the light from the input to the tissue in a predetermined geometry as discussed above. The optical fibers can be arranged in a pattern that targets certain layers of the tissue that contain good glycosylated collagen information. The spacing and placement of the input and output fibers can be arranged in an optimal manner to achieve effective depth targeting. In addition to the use of optical fibers, the tissue sampling interface can use a non-fiber based arrangement that places a pattern of input and output areas on the surface of the tissue when using diffuse reflectance. Proper masking of the non-fiber based tissue sampling interface can ensure that the input light travels a minimum distance in the tissue and contains valid glycosylated collagen information. Finally, the tissue sampling interface can be used to control the temperature of the tissue in a predetermined fashion.

The tissue sampling subsystem can employ an ergonomic apparatus or cradle 210 that positions the tissue over the sampling interface 206 in a reproducible manner. An ergonomic apparatus 210 is depicted in FIG. 8. In the case of sampling the underside of the forearm, an ergonomic cradle design can ensure good contact with the sampling interface. The ergonomic cradle 210 includes a base 221 having an opening 223 therethrough. The opening is sized for receiving the sample head 216 therein to position the sampling surface 204 generally coplanar with an upper surface 225 of the base 221. The ergonomic cradle 210 references the elbow and upper arm of the subject via a bracket 222 in conjunction with a float-to-fit handgrip 224 to accurately position the forearm on the tissue sampling interface. Careful attention to the ergonomics of the tissue sampling interface can minimize sampling error. Errors in sampling the tissue can be a major source of reduced accuracy for the non-invasive classification of disease state.

The ergonomic cradle 210 can be designed such that the forearm of the subject is reliably located over the sample head 216. The bracket 222 forms an elbow rest that sets the proper angle between the upper arm and the sampling head 216, and also serves as a registration point for the arm. The adjustable hand rest 224 is designed to hold the fingers in a relaxed manner. The hand rest position can be adjusted for each subject to accommodate different forearm lengths. A lifting mechanism can be included which raises and lowers the cradle periodically during sampling to break and reform the tissue interface. Reformation of the interface can facilitate reduction of sampling errors due to the rough nature and inhomogeneity of the skin.

The image formed by the output of the tissue sampling subsystem is typically an order of magnitude smaller in size than its input. This input image to output image ratio can match the throughput supported by the FTIR spectrometer while maximizing the overall system signal to noise ratio. The output of the tissue sampling subsystem 200 transfers the portion of the light not absorbed by the tissue that has traveled an acceptable path through the tissue to the input of the FTIR spectrometer subsystem 400. The output of the tissue sampling subsystem 200 can use any combination of refractive and/or reflective optics to produce a collimated beam that will be modulated by the FTIR spectrometer. The diffusely reflected light collected by the output fibers 207 of the sampler head 216 can be collimated by a plano-aspheric lens made of ZnSe. The design of the lens can be such that the collimated beam has less than five degrees of divergence. This lens 228 is schematically depicted in FIG. 4 as part of the FTIR spectrometer subsystem 400. The collimating lens 228 produces a beam with low optical distortion that serves as the proper input to the FTIR spectrometer discussed below.

Figure 9:
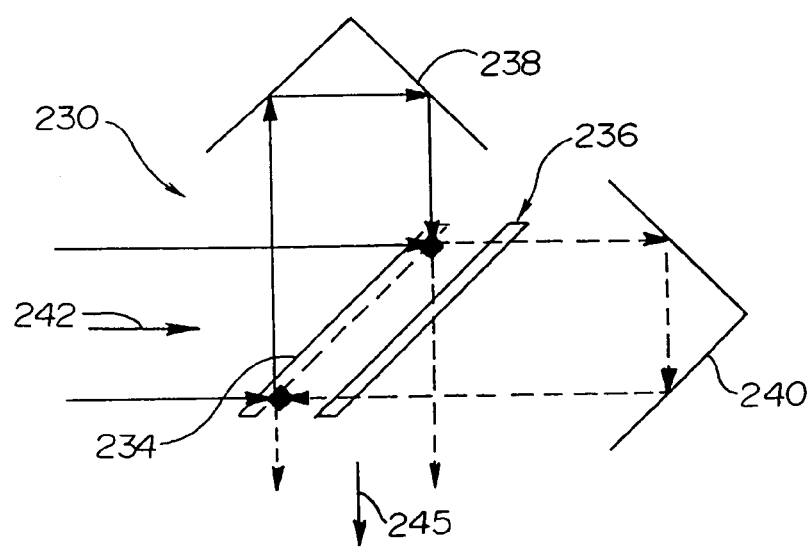
FIG. 9 is a simplified schematic view of an FTIR spectrometer.

As shown in FIG. 4, the FTIR spectrometer subsystem 400 includes a spectrometer 230 that modulates the sufficiently collimated light from the tissue sampling subsystem 200 to create an interferogram which is received by a detector 232. The interferogram spatially encodes the near-infrared spectrum collected by the tissue sampling subsystem. FIG. 9 schematically depicts one embodiment of an FTIR spectrometer 230 which includes a beamsplitter 234 and compensator optics 236, a fixed retro-reflector 238 and a moving retro-reflector 240. The collimated input light 242 impinges on the beamsplitter optic 234 and is partially reflected and partially transmitted by the coating on the back surface of the beamsplitter 234. The reflected light passes back through the beamsplitter optic 234 and reflects off the fixed retro-reflector 238 and back to the beamsplitter 234. The transmitted light passes through the compensator optic 236 and reflects off the moving retro-reflector 240 and back to the beamsplitter 234. The transmitted and reflected portions of the light recombine at the beamsplitter to create an interference pattern or interferogram. The amount of constructive and/or destructive interference between the transmitted and reflected beams is dependent on the spectral content of the collimated input beam 242 and on the optical path difference between the fixed retro-reflector 238 and the moving retro-reflector 240.

In one embodiment, the non-invasive FTIR spectrometer subsystem 400 utilizes an FTIR spectrometer 230 manufactured by Bomem. This spectrometer utilizes a single plate that contains beamsplitter and compensator functions. In addition, cube corners are used as the end mirrors and both cube corners are moved on a wishbone suspension to create the optical path difference and the subsequent interference record. The Bomem WorkIR™ FTIR spectrometer achieves thermal stability and spectral complexity performance for making non-invasive diabetes disease state analysis with near-infrared spectroscopy. The FTIR spectrometer modulates the collimated light from the tissue sampler to spatially encode the near-infrared spectrum into an interferogram. The spectral resolution of the interferogram can be in the range of 7.5 to 64 wavenumbers. The range of spectral resolution is 30–50 wavenumbers. The interferometer will produce either a single-sided or a double-sided interferogram; the double-sided interferogram can achieve a higher SNR. The resulting interferogram can be passed to a condensing lens 244, as shown in FIG. 4, and this lens focuses the light onto the detector 232. The condensing lens 244 is a double convex design with each surface being aspherical in nature. The lens material is ZnSe. The detector 232 can be a thermo-electrically cooled, 1 mm diameter, extended range, InGaAs detector that is sensitive to light in the 1.2 to 2.5 µm region of the spectrum. The detector 232 converts the optical interferogram into its electrical equivalent.

Any photodetector that satisfies basic sensitivity, noise and speed requirements can be used with the present invention. A suitable photodetector can have a shunt resistance greater than 6000 ohms, a terminal capacitance less than 6 nano farads and a minimum photosensitivity of 0.15 amps per watt over the 1.2 to 2.5 micron spectral region. In addition, the photodetector can have a cut-off frequency greater than or equal to 1000 hertz. The shunt resistance of the photodetector defines the Johnson or thermal noise of the detector. The photodetector's performance can be improved by making the Johnson noise of the detector be low relative to the photon flux at the detector. The terminal capacitance governs the cut-off frequency of the photodetector and can also be a factor in the high frequency noise gain of the photodetector amplifier. The photo sensitivity can directly impact the signal portion of the SNR equation.

The optical interferogram can be converted to an electrical signal by the detector and this signal received by the data acquisition subsystem 500. The data acquisition subsystem 500 amplifies and filters the electrical signal from the detector and then converts the resulting analog electrical signal to its digital representation with an analog to digital converter. The analog electronics and ADC can support the high SNR and linearity inherent in the interferogram. The data acquisition subsystem 500 supports at least 100 dbc of SNR plus distortion. The data acquisition subsystem 500 produces a digitized interferogram that has uniform spatial displacement between samples. The data acquisition subsystem 500 also receives the reference laser signal from the FTIR spectrometer subsystem 400. Both the near-infrared signal and the reference laser can be digitized by a 24-bit delta-sigma ADC operated at 96 kilohertz. The digital output of the ADC can be processed by a signal processor to produce an interferogram that is sampled at constant spatial intervals. The interferograms can be passed to the embedded computer subsystem 600 for further processing, as discussed below. Traditionally, the zero crossings of the reference laser are utilized to mark constant spatial intervals for sampling of the interferogram. The zero crossings of the reference laser are spaced at intervals equal to half the wavelength of the monochromatic light emitted by the laser.

Further, the data acquisition subsystem 500 can utilize a constant time sampling, dual channel, delta-sigma analog-to-digital converter (ADC) to support the SNR and photometric accuracy requirements of the present disease state analysis. The delta-sigma ADC can support sampling rates of over 100 kHz per channel, have a dynamic range in excess of 117 dbc and have total harmonic distortion less than −105 dbc.

There are other types of data acquisition systems for the FTIR spectrometer and photodetector that are known in the art and could be employed in the present invention if they provide the following performance characteristics for constant spatial sampling, dynamic range, SNR, harmonic distortion and sampling speed. There is an allowable error in determining the constant spatial sampling intervals of the interferogram, and the spatial sampling interval determination should have a maximum spatial sampling jitter of +/−25 nanometers in order to preserve a SNR of 100 dbc at 1.2 microns (8000 cm$^{-1}$). Levels of spatial sampling jitter greater than +/−25 nanometers can introduce frequency modulation artifacts into the spectra and can degrade the signal. In addition, the data acquisition subsystem can support a dynamic range of at least 100 dbc, a SNR of 90 dbc and have total harmonic distortion less than 90 dbc. Finally, the ADC of the data acquisition subsystem can be able to sample at speeds of 5,000 samples per second or greater in order to support a minimum FTIR moving mirror scanning speed of 0.25 centimeters per second.

The constant time sampling data acquisition subsystem 500 has several distinct advantages over the more traditional methods of acquiring interferograms from an FTIR spectrometer. These advantages include greater dynamic range, lower noise, reduced spectral artifacts, detector noise limited operation and simpler and less expensive analog electronics. In addition, the constant time sampling technique improves the vibration immunity of the FTIR because it can digitally compensate for delay mismatches between the laser reference and infrared detectors and can back out the non-ideal aspects of the electronics' transfer function. The constant time sampling technique can require increased computational and memory requirements to translate the constant time samples of the interferogram to constant spatial samples. A high performance digital signal processor (DSP) can provide the additional computation and memory requirements to attain the performance enhancements of the constant time sampling technique.

The data acquisition subsystem passes the digitized, constant spatially sampled interferograms to the embedded computer subsystem 600 for further processing. The embedded computer subsystem 600 converts the stream of interferograms to single beam spectra by windowing the interferogram, performing phase correction of the windowed interferogram and then taking the Fourier transform of the windowed and phase corrected interferogram. Mertz and power phase correction methods can be used. The power phase correction method can be simpler to implement, but results in noise that has nonzero mean and is larger in magnitude by a factor of 1.414. The Mertz phase correction method can be more complicated but can produce noise with zero mean and does not inject noise from the imaginary portion of the complex spectrum. The Mertz method can result in spectra with higher photometric accuracy. When using multivariate analysis techniques, both phase correction methods result in equivalent prediction performance.

After converting the interferograms to single beam spectra, the embedded computer system can check the single beam spectra for outliers or bad scans. An outlier sample or bad scan is one that violates the hypothesized relationship between the measured signal and the properties of interest (i.e., glycosylated collagen measurement in human tissue). Examples of outlier conditions include conditions where the calibrated instrument is operated outside of the specified operating ranges for ambient temperature, ambient humidity, vibration tolerance, component tolerance, power levels, etc. In addition, an outlier can occur if the composition or concentration of the sample is different than the composition or concentration range of the samples used to build the calibration model. Any outliers or bad scans can be deleted and the remaining good spectra are averaged together to produce an average single beam spectrum for the measurement. The average single beam spectrum can be converted to absorbance by taking the negative base 10 logarithm (log10) of the spectrum. The absorbance spectrum can be scaled by a single beam spectrum to renormalize the noise. The resulting scaled absorbance spectrum can then have calibration maintenance and/or calibration transfer algorithms applied to it. Calibration maintenance techniques are discussed in detail below and in commonly assigned U.S. patent application Ser. No. 09/832,608, filed on Apr. 11, 2001, and entitled "Optically Similar Reference Samples and Related Methods for Multivariate Calibration Models Used in Optical Spectroscopy", incorporated herein by reference. Calibration transfer techniques are disclosed in commonly assigned U.S. patent application Ser. No. 09/563,865, filed May 3, 2000, entitled "Method and Apparatus for Spectroscopic Calibration Model Transfer", incorporated herein by reference.

An algorithm stored in the embedded computer subsystem can then be applied to the scaled absorbance spectrum, as calibrated, to determine disease state. After generating a disease state prediction, the embedded computer subsystem 600 will report the predicted value 830 to the subject. Optionally, the embedded computer subsystem 600 can report the level of confidence in the goodness of the predicted value. If the confidence level is low, the embedded computer subsystem 600 can withhold the predicted disease state and ask the subject to retest. The classification can be reported visually on a display, by audio and/or by printed means. Additionally, the predicted disease state can be stored in memory in order to form a historical record of the analysis.

The embedded computer subsystem 600 can include a central processing unit (CPU), memory, storage, a display and a communication link. An example of a CPU is the Intel Pentium microprocessor. The memory can be, for example, static random access memory (RAM) and/or dynamic random access memory. The storage can be accomplished with non-volatile RAM or a disk drive. A liquid crystal display is an example of the type of display that would be used in the device. The communication link can be a high speed serial link, an Ethernet link or a wireless communication link. The embedded computer subsystem can produce disease state predictions from the received and processed interferograms, perform calibration maintenance, perform calibration transfer, run instrument diagnostics, store a history of past analysis and other pertinent information, and in some embodiments, can communicate with remote hosts to send and receive data and new software updates.

The embedded computer system can also contain a communication link that allows transfer of the subject's prediction records and the corresponding spectra to an external database. In addition, the communication link can be used to download new software to the embedded computer, update the multivariate calibration model, provide information to the subject to enhance the management of their disease, etc. The embedded computer system is very much like an information appliance. Examples of information appliances include personal digital assistants, web-enabled cellular phones and handheld computers.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method for indicating diabetes in an individual utilizing tissue optical information from the individual comprising the steps of:

obtaining tissue optical information from at least one wavelength from the individual, the tissue optical information including information from at least one wavelength indicative of glycosylated collagen content in the tissue;

providing a multivariate algorithm relating optical information to glycosylated collagen in the tissue; and applying the multivariate algorithm to the tissue optical information from the individual to indicate diabetes.

2. The method of claim 1, wherein the at least one wavelength indicative of glycosylated collagen content is selected from following bands: 2240 nm–2300 nm, 2145 nm–2200 nm, 2025 nm–2060 nm, and 1670 nm–1745 nm.

3. The method of claim 1, wherein the tissue optical information includes a second wavelength indicative of glycosylated collagen content in the tissue and the multivariate algorithm includes a second factor dependent on information from the second wavelength indicative of glycosylated collagen content.

4. The method of claim 3, wherein the second wavelength indicative of glycosylated collagen content is selected from the following bands: 2240 nm–2300 nm, 2145 nm–2200 nm, 2025 nm–2060 nm, and 1670 nm–1745 nm.

5. The method of claim 1, wherein the at least one wavelength indicative of glycosylated collagen content is greater than 500 nm and less than 3300 nm.

6. The method of claim 1, wherein the multivariate algorithm has at least one factor dependent on subject characteristics.

7. The method of claim 1, wherein the multivariate algorithm has at least one factor dependent on environmental risk factors.

8. A method for classifying an individual as non-diabetic, diabetic or indicating a probability of becoming diabetic utilizing tissue optical information from other individuals having known disease states, the tissue optical information including information from at least one wavelength indicating glycosylated collagen content in the tissue, the method comprising the steps of:

obtaining tissue optical information from the at least one wavelength from the individual, the tissue optical information including information indicating glycosylated collagen content in the tissue; and using a multivariate algorithm to classify the individual as diabetic, non-diabetic or indicating a probability of becoming diabetic, the multivariate algorithm relating tissue optical information to glycosylated collagen content in the tissue.

9. The method of claim 8, wherein the at least one wavelength indicative of glycosylated collagen content is selected from the following bands: 2240 nm–2300 nm, 2145 nm–2200 nm, 2025 nm–2060 nm, and 1670 nm–1745 nm.

10. The method of claim 8, wherein the tissue optical information includes information from a second wavelength indicative of glycosylated collagen content in the tissue and the multivariate algorithm includes a second factor dependent on information from the second wavelength indicative of glycosylated collagen content.

11. The method of claim 10, wherein the second wavelength indicative of glycosylated collagen content is selected from the following bands: 2240 nm–2300 nm, 2145 nm–2200 nm, 2025 nm–2060 nm, and 1670 nm–1745 nm.

12. An apparatus for determining the probability, progression or level of diabetes, the apparatus comprising:

a light source that generates light, including light at at least one wavelength indicating glycosylated collagen in tissue;

a sampling means for coupling the light to tissue and collecting the light modified by the tissue;

a spectrometer coupled to the sampling means for measuring the optical information of the modified light collected from the tissue, the optical information including information indicating glycosylated collagen content in the tissue; and means for processing the optical information to determine the probability, progression or level of diabetes, the means including an algorithm relating optical information to glycosylated collagen in tissue.

13. The apparatus of claim 12, wherein the at least one wavelength indicative of glycosylated collagen is selected from the following bands: 2240 nm–2300 nm, 2145 nm–2200 nm, 2025 nm–2060 nm, and 1670 nm–1745 nm.

14. The apparatus of claim 12, wherein the light source generates light including a second wavelength indicative of glycosylated collagen content in the tissue and the algorithm includes a second factor dependent on optical information at the second wavelength indicative of glycosylated collagen content.

15. An apparatus for non-invasively detecting the probability, progression or level of diabetes in human tissue by near-infrared spectroscopy comprising:

an illumination subsystem which generates near infrared light including at least one wavelength indicating glycosylated collagen content in human tissue;

a tissue sampling subsystem optically coupled to the illumination subsystem which receives at least a portion of the infrared light, the tissue sampling subsystem including means for irradiating human tissue with at least a portion of the received infrared light and collecting at least a portion of the light diffusely reflected from the human tissue;

an FTIR spectrometer subsystem optically coupled to the tissue sampling subsystem to receive at least a portion of the light diffusely reflected from the tissue, the FTIR spectrometer subsystem including a spectrometer that creates an interferogram, the FTIR spectrometer subsystem further including a detector which receives the interferogram and converts the interferogram to an electrical representation;

a data acquisition subsystem which receives the electrical representation of the interferogram, the data acquisition subsystem including means for amplifying and filtering the electrical representation and converting a resulting electrical signal to its digital representation; and a computing subsystem for receiving the digital representation and further including a multivariate algorithm for detecting the probability, progression or level of diabetes, wherein the algorithm relates the digital representation to glycosylated collagen content in the human tissue.

16. The apparatus of claim 15, wherein the at least one wavelength indicative of glycosylated collagen content is selected from the following bands: 2240 nm–2300 nm, 2145 nm–2200 nm, 2025 nm–2060 nm, and 1670 nm–1745 nm.

17. The apparatus of claim 15, wherein the illumination subsystem generates light including a second wavelength indicative of glycosylated collagen content in the tissue and the multivariate algorithm includes a second factor dependent on the measurements at the second wavelength indicative of glycosylated collagen content.

18. A method for determining glycosylated collagen in an individual utilizing tissue optical information from the individual, comprising the steps of:

obtaining tissue optical information from at least one wavelength from the individual, the tissue optical information including information from at least one wavelength indicative of glycosylated collagen in the tissue;

providing a multivariate algorithm relating optical information to glycosylated collagen; and applying the multivariate algorithm to the tissue optical information from the individual to determine glycosylated collagen in the individual.

19. A method for indicating diabetes in an individual utilizing tissue optical information from the individual comprising the steps of:

obtaining tissue optical information from at least one wavelength from the individual using near-infrared spectroscopy, the tissue optical information including information from at least one wavelength indicative of glycosylation end product content in the tissue, wherein the at least one wavelength indicative of glycosylation end product content is selected from following bands: 2240 nm–2300 nm, 2145 nm–2200 nm, 2025 nm–2060 nm, and 1670 nm–1745 nm;

providing a multivariate algorithm relating optical information to glycosylation end products in the tissue; and applying the multivariate algorithm to the tissue optical information from the individual to indicate diabetes.

20. The method of claim 19, wherein the tissue optical information includes a second wavelength indicative of glycosylation end product content in the tissue and the multivariate algorithm includes a second factor dependent on information from the second wavelength indicative of glycosylation end product content, wherein the second wavelength indicative of glycosylation end product content is selected from the following bands: 2240 nm–2300 nm, 2145 nm–2200 nm, 2025 nm–2060 nm, and 1670 nm–1745 nm.

21. The method of claim 19, wherein the multivariate algorithm has at least one factor dependent on subject characteristics.

22. The method of claim 19, wherein the multivariate algorithm has at least one factor dependent on environmental risk factors.

23. A method for classifying an individual as non-diabetic, diabetic or indicating a probability of becoming diabetic utilizing tissue optical information from other individuals having known disease states, the tissue optical information including information from at least one wavelength indicating glycosylation end product content in the tissue, wherein the at least one wavelength indicative of glycosylation end product content is selected from the following bands: 2240 nm–2300 nm, 2145 nm–2200 nm, 2025 nm–2060 nm, and 1670 nm–1745 nm, the method comprising the steps of:

obtaining tissue optical information from the at least one wavelength from the individual using near-infrared spectroscopy, the tissue optical information including information indicating glycosylation end product content in the tissue; and using a multivariate algorithm to classify the individual as diabetic, non-diabetic or indicating a probability of becoming diabetic, the multivariate algorithm relating tissue optical information to glycosylation end product content in the tissue.

24. The method of claim 23, wherein the tissue optical information includes information from a second wavelength indicative of glycosylation end product content in the tissue and the multivariate algorithm includes a second factor dependent on information from the second wavelength indicative of glycosylation end product content, wherein the second wavelength indicative of glycosylation end product content is selected from the following bands: 2240 nm–2300 nm, 2145 nm–2200 nm, 2025 nm–2060 nm, and 1670 nm–1745 nm.

25. An apparatus for determining the probability, progression or level of diabetes, the apparatus comprising:

a light source that generates near-infrared light, including light at at least one wavelength indicating glycosylation end products in tissue, wherein the at least one wavelength indicative of glycosylation end products is selected from the following bands: 2240 nm–2300 nm, 2145 nm–2200 nm, 2025 nm–2060 nm, and 1670 nm–1745 nm;

a sampling means for coupling the light to tissue and collecting the light modified by the tissue;

a near-infrared spectrometer coupled to the sampling means for measuring the optical information of the modified light collected from the tissue, the optical information including information indicating glycosylation end product content in the tissue; and means for processing the optical information to determine the probability, progression or level of diabetes, the means including an algorithm relating optical information to glycosylation end products in tissue.

26. The apparatus of claim 25, wherein the light source generates light including a second wavelength indicative of glycosylated collagen content in the tissue and the algorithm includes a second factor dependent on optical information at the second wavelength indicative of glycosylated collagen content.

27. An apparatus for determining the probability, progression or level of diabetes, the apparatus comprising:

a light source that generates light, including light at a first wavelength indicative of glycosylation end products in tissue, and at a second wavelength indicative of glycosylation end products in tissue, wherein the first wavelength indicative of glycosylation end products is selected from the following bands: 2240 nm–2300 nm, 2145 nm–2200 nm, 2025 nm–2060 nm, and 1670 nm–1745 nm;

a sampling means for coupling the light to tissue and collecting the light modified by the tissue;

a spectrometer coupled to the sampling means for measuring the optical information of the modified light collected from the tissue, the optical information including information indicating glycosylation end product content in the tissue; and means for processing the optical information to determine the probability, progression or level of diabetes, the means including an algorithm relating optical information to glycosylation end products in tissue.

* * * * *